United States Patent [19]

Ness

[11] 4,133,307
[45] Jan. 9, 1979

[54] TRACTION DEVICE

[76] Inventor: Richard A. Ness, Fergus Falls, Minn. 56537

[21] Appl. No.: 795,174

[22] Filed: May 9, 1977

[51] Int. Cl.² .................................................. A61H 1/02
[52] U.S. Cl. ................................... 128/75; 128/349 R
[58] Field of Search ............... 128/75, 2 R, 25, 2 W, 128/303 R, 155, 156, DIG. 26, 349 R; 24/DIG. 11; 248/205 A

[56] References Cited

U.S. PATENT DOCUMENTS

| | | | |
|---|---|---|---|
| 2,169,259 | 8/1939 | Lakin | 24/243 R |
| 2,421,193 | 5/1947 | Gardner | 128/335 |
| 3,019,791 | 2/1962 | Limbeck | 128/249 R |
| 3,134,152 | 5/1964 | Pei | 128/335 |
| 3,221,735 | 12/1965 | Goodman | 128/75 |
| 3,430,300 | 3/1969 | Doan | 128/349 R |
| 3,613,679 | 10/1971 | Bijou | 128/156 |
| 3,677,250 | 7/1972 | Thomas | 128/348 |
| 3,726,280 | 4/1973 | Lacount | 128/349 |
| 4,057,066 | 11/1977 | Taylor | 128/DIG. 26 |

Primary Examiner—Robert W. Michell
Assistant Examiner—Arthur S. Rose
Attorney, Agent, or Firm—Merchant, Gould, Smith, Edell, Welter & Schmidt

[57] ABSTRACT

An elongated elastic strip for holding in traction or tension a relatively movable member, such as a catheter of the balloon type used to provide hemostasis. The elastic strip has enlarged end portions for attachment respectively to the relatively movable member and to a relatively stationary member or portion. A measuring device on the elastic strip indicates the degree of tension applied to the movable member.

3 Claims, 6 Drawing Figures

U.S. Patent
Jan. 9, 1979
4,133,307
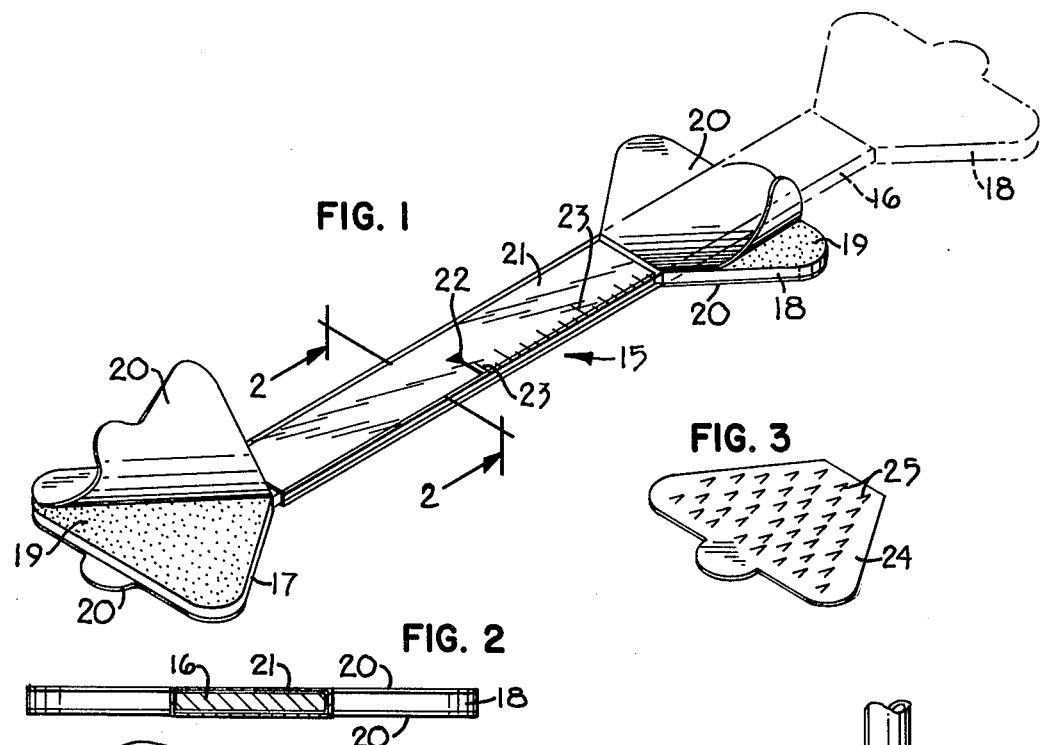
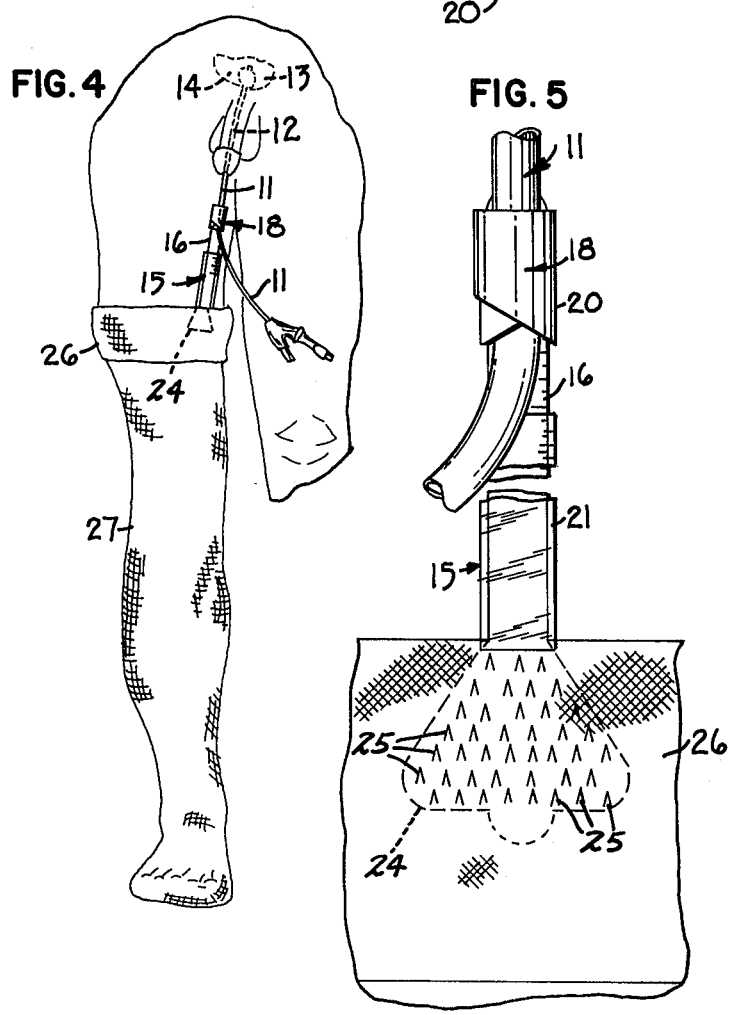

TRACTION DEVICE

BACKGROUND OF THE INVENTION

This invention relates generally to the application of tension or traction of a movable member or portion thereof, and more particularly to the application of traction to a balloon catheter when used in postoperative treatment in the transurethral resection of the prostate gland. During the postoperative period, the inner end portion of the balloon catheter is disposed in the patient's bladder for removal of urine, the balloon portion of the catheter being held against the entrance of the urethra by placing the catheter in traction. By this means, blood is prevented from entering the bladder where clotting of the blood may occur, causing complications and preventing free flow of urine from the bladder.

Heretofore, after prostate resection, a balloon catheter, common known as a "Foley" catheter, has been maintained by fastening an outer end portion thereof to the patient's thigh by means of a length of surgical adhesive tape applied to the catheter and to the skin of the patient. In many cases, contact of the tape with the skin has resulted in so-called "tape burn" and other side effects, particularly among patients allergic to the material of the tape. Further, discomfort has been experienced by patients having hirsute thighs, during removal of the adhesive tape therefrom. In addition, the amount or degree of tension applied to the catheter has been heretofore a matter of guess work and difficult to establish with accuracy, often resulting in either extreme discomfort to the patient or leakage of fluid from the bladder to the area of resection.

SUMMARY OF THE INVENTION

The traction device of this invention involves an elongated strip of elastic material of given width and end portions at the opposite ends of the strip of greater width than said strip and having normally flat opposite sides. On one of said flat sides of one of said end portions is an adhesive coating for adhesive engagement with an object to which traction is to be applied. The traction device further includes fastener means on the other one of said end portions for securing said other one of the end portions substantially against movement longitudinally of said strip, and means including an elongated inelastic member secured at one end adjacent one of said end portions and extending along said strip for measuring elongation of said strip when the strip is subject to tensile stress, said strip and elastic member having tension measuring indicia thereon.

BRIEF DESCRIPTION OF THE DRAWINGS

FIG. 1 is a view in perspective of a traction device produced in accordance with this invention;

FIG. 2 is an enlarged transverse section taken on the line 2—2 of FIG. 1;

FIG. 3 is a view in perspective of an anchoring element;

FIG. 4 is a fragmentary view in front elevation, showing the traction device of this invention in use;

FIG. 5 is an enlarged view corresponding to a portion of FIG. 4, some parts being broken away; and FIG. 6 is a view in side elevation of the traction device.

DETAILED DESCRIPTION OF THE PREFERRED EMBODIMENT

As indicated above, one of the primary uses of the traction device of this invention lies in connection with the imparting of traction to a balloon or "Foley" catheter in providing hemostasis after transurethral resection of the prostate gland. A catheter is indicated generally at 11, and in the more or less diagrammatic illustration of FIG. 4, is shown as extending through the urethra 12 and into the interior of the bladder, shown by dotted lines in FIG. 4 and indicated at 13. Adjacent its inner end, the catheter is provided with an inflatable portion or balloon 14 that is inflated after insertion by suitable fluid introduced thereto through a longitudinal passage in the catheter. Fluid is drained from the bladder 13 through another longitudinal passage in the catheter 11. The balloon or Foley catheter is well known and further detailed description thereof is omitted in the interest of brevity. In use, the catheter 11 is placed in traction to hold the balloon 14 against the wall of the bladder 13 to prevent bleeding into the interior of the bladder 13.

The traction device of this invention, indicated generally at 15, comprises an elongated flat strip 16 of elastic material such as rubber or other suitable latex compounds, and having end portions 17 and 18 at the opposite ends thereof. It will be noted that the end portions 17 and 18 are substantially greater in width than the strip 16, the end portions 17 and 18 being preferably generally triangular in shape. The opposite generally flat sides of the end portions 17 and 18 are coated with pressure sensitive adhesive material, indicated at 19, these sides being normally covered with removable protective tabs 20.

An elongated inelastic member 21 is shown as being in the nature of a cross sectionally rectangular transparent tube that loosely encompasses the strip 16 and which is rigidly secured at one end to the flat strip 16 adjacent the end portion 17 thereof, by adhesives or other suitable means. The inelastic member 22 may be made from any suitable transparent material, such as synthetic plastics or, if desired, may be provided with an opening, not shown, intermediate its ends, through which the underlying portion of the strip 16 may be seen. The strip 16 has imprinted thereon a transversely extending line or index mark 22 that cooperates with a series of graduations 23 on the inelastic member 21 to measure the amount or degree of tension to which the strip 16 is subject when stretched to a given length. In FIG. 1, the traction device 15 is shown in a normal condition by full lines, and in a stretched condition of the strip 16 by broken lines.

In FIG. 3, a plate-like fastener member 24 is shown, the fastener member 24 being preferably of the same shape and size as either of the end portions 17 or 18. As shown, the fastener member is provided with a series of anchoring elements in the form of angularly outwardly projecting barbs 25 that are adapted to easily pierce woven or knitted textile fabric. The fastener member 24 may be made of lightweight sheet metal or plastic material and is particularly adapted to be secured to the end portion 17 by being pressed against an adhesive coating 19 thereon when the protective tab 20 is removed.

When the above traction device 15 is to be used to place a balloon catheter 11 in traction, after the catheter has been properly inserted and the balloon 14 inflated, one of the protective tabs 20 on the end portion 18 is removed, and the end portion 18 wrapped around a portion of the catheter 11, as shown in FIGS. 4-6, the adhesive coating 19 causing the device 15 to be securely adhered to the catheter 11. Then, with the fastener member 24 adhered to the end portion 17, with the barbs 25 projecting forwardly or outwardly with respect to the upper leg or thigh of the patient, the end portion 17 is moved downwardly, causing the flat strip 16 to be stretched to place the upper portion of the catheter between the bladder 13 and end portion 18 under a given tension. The degree of tension or traction is indicated by the location of the index mark 22 with respect to the graduations 23. With proper traction applied to the catheter 11, the barbs 25 of the fastener member 24 are inserted in the cuff portion 26 at the upper end of a surgical stocking 27, as shown in FIGS. 4-6. The stocking 27 is of the type that is used in standard procedures associated with urological operations and provides a convenient and readily available anchor for the traction device.

In the event that a patient is not adversely affected by the pressure sensitive adhesive material, the fastener member 24 need not be used. In this event, the protective tab 20 on the front or outer side of the end portion 17 remains adhered thereto, while the tab 20 on the opposite side of the end portion 17 is removed and the end portion 17 being adhered directly to the skin of the leg.

In the event that a greater amount of tension is needed than will be afforded by a single traction device 15, two or more of the devices may be used in stacked relationship. In other words, a second device 15 may be adhered to a first device by merely removing the tabs 20 from the end portions 17 and 18 of one device and the tabs 20 from the front surfaces of the end portions 17 and 18 from a second device and adhering corresponding end portions 17 and 18 to each other, as shown by dotted lines in FIG. 6.

The traction device of this invention is capable of various other uses in the surgical field. For instance, by adhering fastener members 24 to both end portions 17 and 18, the device may be used to apply given traction to opposite ends of a bandage wrapped partially around a portion of the patient's body to be bandaged. In other cases, the device may be used to bridge an incision, and to place the patient's skin at opposite sides of the incision under sufficient traction to yieldingly hold the same closed.

While I have shown and described a preferred embodiment of a traction device, it will be understood that the same is capable of modification without departure from the spirit and scope of the invention, as defined in the claims.

What is claimed is:

1. A traction device comprising:
   (a) an elongated strip of elastic material of given width;
   (b) end portions at the opposite ends of said strip of greater width than said strip and having normally flat opposite sides;
   (c) an adhesive coating on one of said flat sides of one of said end portions for adhesive engagement with an object to which traction is to be applied;
   (d) adhesive coatings on the opposite sides of the other one of said end portions;
   (e) a fastening member being adhered in use to a selected one of said opposite sides of said other one of said end portions and having anchoring elements thereon capable of piercing textile fabric when said fastener member is pressed into engagement with said fabric;
   (f) and means including an elongated inelastic member anchored at one end adjacent one of said end portions and extending along said strip for indicating the amount of elongation of said strip when the strip is subjected to tensile stress, said strip and inelastic member having tension measuring indicia thereon.

2. The traction device defined in claim 1 in which said elastic strip has a flat surface substantially coplanar with said flat sides, said inelastic member having a portion overlying said flat surface, said indicia including an index mark on said elastic strip and a series of graduations on said inelastic member.

3. The traction device defined in claim 2 in which said inelastic member comprises a flat tube encompassing said elastic strip, said tube being at least in part transparent to render said index mark visible therethrough.

* * * * *